United States Patent
Hepler et al.

(10) Patent No.: US 10,555,899 B2
(45) Date of Patent: Feb. 11, 2020

(54) LONG-ACTING NON-AQUEOUS INJECTABLE FORMULATIONS AND USE THEREOF

(71) Applicant: PIEDMONT ANIMAL HEALTH, LLC, Greensboro, NC (US)

(72) Inventors: Douglas I. Hepler, Greensboro, NC (US); Gail L. Dempsey, Greensboro, NC (US); Dorothea Erxleben, Greensboro, NC (US)

(73) Assignee: Piedmont Animal Health, LLC, Greensboro, NC (US)

( * ) Notice: Subject to any disclaimer, the term of this patent is extended or adjusted under 35 U.S.C. 154(b) by 0 days.

(21) Appl. No.: 16/000,670

(22) Filed: Jun. 5, 2018

(65) Prior Publication Data

US 2018/0344629 A1 Dec. 6, 2018

Related U.S. Application Data

(60) Provisional application No. 62/515,347, filed on Jun. 5, 2017.

(51) Int. Cl.
| | | |
|---|---|---|
| A61K 31/485 | (2006.01) | |
| A61K 47/10 | (2017.01) | |
| A61K 47/14 | (2017.01) | |
| A61K 47/28 | (2006.01) | |
| A61P 29/02 | (2006.01) | |
| A61K 9/00 | (2006.01) | |
| A61K 9/107 | (2006.01) | |

(52) U.S. Cl.
CPC ............ *A61K 9/0019* (2013.01); *A61K 9/107* (2013.01); *A61K 31/485* (2013.01); *A61K 47/10* (2013.01); *A61K 47/14* (2013.01); *A61K 47/28* (2013.01); *A61P 29/02* (2018.01)

(58) Field of Classification Search
CPC ........ A61K 9/00; A61K 31/485; A61K 47/10; A61K 47/14; A61K 47/28; A61P 29/02
See application file for complete search history.

(56) References Cited

U.S. PATENT DOCUMENTS

| | | |
|---|---|---|
| 9,248,098 B2 | 2/2016 | Didsbury et al. |
| 2008/0096910 A1 | 4/2008 | Guarnieri |
| 2013/0203796 A1 | 8/2013 | Norton et al. |
| 2016/0220505 A1 | 8/2016 | Krayz et al. |

OTHER PUBLICATIONS

International Search Report dated Sep. 7, 2018, regarding PCT/US2018/036034.

*Primary Examiner* — Zohreh A Fay
(74) *Attorney, Agent, or Firm* — DLA Piper LLP (US)

(57) ABSTRACT

Provided herein are long-acting, non-aqueous pharmaceutically acceptable compositions of active ingredients for subcutaneous injection, in particular analgesics such as buprenorphine.

17 Claims, 2 Drawing Sheets

LONG-ACTING NON-AQUEOUS INJECTABLE FORMULATIONS AND USE THEREOF

CROSS-REFERENCE TO RELATED APPLICATION(S)

This application claims benefit of priority under 35 U.S.C. § 119(e) of U.S. Ser. No. 62/515,347 filed Jun. 5, 2017, the entire contents of which is incorporated herein by reference in its entirety.

BACKGROUND OF THE INVENTION

Field of the Invention

The invention relates generally to long-acting, non-aqueous, subcutaneously injectable formulations and more specifically to a long-acting analgesic formulation, especially for use in mammals.

Background Information

Conventional long-acting injections consist either of lipophilic drugs in aqueous solvents as suspensions or of lipophilic drugs dissolved in vegetable oils. In the suspension formulations, the rate-limiting step of drug absorption is the dissolution of drug particles in the formulation or in the tissue fluid surrounding the drug formulation. Poorly water-soluble salt formulations can be used to control the dissolution rate of drug particles to prolong the absorption. However, several other factors such as injection site, injection volume, the extent of spreading of the depot at the injection site, and the absorption and distribution of the oil vehicle per se might affect the overall pharmacokinetic profile of the drug.

Biodegradable microsphere systems are also available for use in extended release formulations, made with an appropriate biodegradable polymer. The release of the drug molecule from biodegradable microspheres is controlled by diffusion through the polymer matrix and polymer degradation. A variety of biodegradable polymers for controlled drug delivery intensively studied over the past several decades include polylactides (PLA), polyglycolides (PGA), poly(lactide-co-glycolide) (PLGA), poly(ε-caprolactone) (PCL), polyglyconate, polyanhydrides, polyorthoesters, poly(dioxanone), and polyalkylcyanoacrylates.

An example of a drug for which a long-acting form would be of value, particularly for use in non-human animals such as cats and dogs, is buprenorphine. Buprenorphine is a synthetic opioid drug that is about 30 times more potent than morphine. Opioids present difficulties in dosing for animals, especially in smaller animals and humans. While buprenorphine can be well-tolerated, dosing is critical. If given in too large amounts, buprenorphine can repress the respiratory system, causing unconsciousness, coma, or death. Further, the use of higher doses of buprenorphine would be expected to result in adverse effects to the mammal. Specifically, adverse effects associated with high dose buprenorphine include excessive sedation, respiratory depression, excessive salivation, and nausea. Due to the seriousness of such effects, commercially available buprenorphine products use low dosages repeated often; e.g., every 2 to 6 hours.

For example, a recent clinical trial demonstrated that several cats undergoing ovariohysterectomy may require a second dose of buprenorphine 4 hours after surgery or other onset of pain, especially if an NSAID had not also been administered (see, Steagall, et al., Journal of Veterinary Internal Medicine, 28(3):762-770, 767 (2014)). In humans, the relatively short action of the drug means that multiple doses need to be provided to manage chronic pain (e.g., 72 hours), requiring a prescription allowing for frequent dosing.

An example of an extended-release buprenorphine composition intended to allow for less frequent dosing is disclosed in U.S. Pat. No. 8,461,173. 24-48 hour release from an implantable pellet was achieved. The pellets were developed using cholesterol and triglyceride dissolved in a solvent such as a halogenated solvent and alcohol at a 5:1 ratio, chloroform or methylene chloride, preferably chloroform, to form a liposome or liposphere. Buprenorphine is added to the desired drug loading, the drug and carrier are mixed to form a uniform dispersion, and the solvent removed by evaporation. The resulting dry powder is then compressed or extruded to form pellets.

The manufacturing of such conventional extended release formulations is complex and costly requiring, as noted, added heat, evaporation steps, application of added pressure (e.g., through compression or extrusion) and/or use of significant quantities of organic solvents which could introduce potential toxicity if not completely removed. It is also difficult to appropriately control the release of a drug such as buprenorphine in an injectable dosage form in order to achieve the desired onset and duration of analgesic effects in the target species. Therefore, it would be desirable to have compositions and less complex methods of providing prolonged pain control to a mammal while minimizing the number of administrations/doses that must be given to the mammal.

In addition, it would be useful to have a buprenorphine composition which does not require addition of other analgesics to achieve full control of pain. In this respect, when buprenorphine is used clinically in cats (especially transdermally), the cat is routinely given a dose of a "full agonist" opioid (e.g., morphine, methadone, meperidine, hydromorphone, fentanyl infusion) or even buprenorphine beforehand (i.e., pre-medication). In the perioperative period, buprenorphine is used commonly for premedication in combination with dexmedetomidine or acepromazine for procedures involving mild to moderate pain. Optimal pain relief usually is obtained when buprenorphine is combined with an NSAID, loco-regional anesthesia, or both.

It is therefore desirable to have a modality by which a form of an lipophilic active such as buprenorphine can simply formulated to provide long-acting activity. For example, it would be particularly useful to have a formulation of an analgesic which can be safely provided with long-lasting results, without manufacture or use of a conventional extended release formulation.

SUMMARY OF THE INVENTION

Provided herein is a long-acting, non-aqueous injectable pharmaceutically acceptable composition for administration to humans and mammalian animals, comprising a mixture of:

a) a lipophilic active substance;

b) at least one oleogeneous carrier such as a triglyceride present at 80.0 to 98.0% w/w of the composition, c) cholesterol at 1.0 to 10.0% w/w of the composition, preferably in milled and/or microcrystalline form; and, optionally, d) a preservative such as benzyl alcohol at no more than 1.0% to 5.0% w/w of the composition and/or glyceryl mono-, di- or tristearate, wherein no liposomes or lipospheres are formed and no water is added to the composition except as may be contributed by a fully or partially hydrated form of a molecule used in the composition.

The invention also provides a long-acting, non-aqueous injectable pharmaceutically acceptable composition for administration to humans and mammalian animals, comprising a mixture of:

a) a lipophilic active substance;

b) at least one triglyceride carrier at about 80.0 to 98.0% w/w of the composition;

c) cholesterol at about 1.0 to 10.0% w/w of the composition, preferably in milled and/or microcrystalline form; and, optionally, d) a preservative such as benzyl alcohol at no more than 1.0% to 5.0% w/w of the composition and/or glyceryl mono-, di- or tristearate, wherein no liposomes or lipospheres are formed and no water is added to the composition except as may be contributed by a fully or partially hydrated form of a molecule used in the composition.

In yet another aspect, the invention provides a long-acting, non-aqueous injectable pharmaceutically acceptable composition for administration to humans and mammalian animals, comprising a mixture of:

a) buprenorphine;

b) caprylic/capric triglyceride at about 80.0 to 98.0% w/w of the composition;

c) cholesterol at about 1.0 to 10.0% w/w of the composition, preferably in milled and/or microcrystalline form; and, optionally, d) a preservative such as benzyl alcohol at no more than 1.0% to 5.0% w/w of the composition and/or glyceryl mono-, di- or tristearate, wherein no liposomes or lipospheres are formed and no water is added to the composition except as may be contributed by a fully or partially hydrated form of a molecule used in the composition.

The long-acting pharmaceutically acceptable composition is prepared without formation of liposomes or lipospheres, addition of water, evaporation of solvent or formation of the composition into conventional extended release forms such as pellets. The active, cholesterol and alcohol components are simply admixed to form a ready-to-inject pharmaceutical suspension composition in which the active is associated with the cholesterol. Remarkably, the resulting composition provides at least up to about 48, 54, 60, 66, 72 hours or greater of active release when administered subcutaneously or intramuscularly via injection.

Without limiting the scope of the invention, it is believed that the extended release properties of the invention are accomplished via an unexpected interaction between a lipophilic active and cholesterol in the composition. The cholesterol, the active and the stearate are proximate to one another in a triglyceride suspension. The particular elements of the composition—including no added water and a relatively large amount (in excess of 85.0% w/w) of triglyceride carrier—are critical to allowing the suspension to form through simple mixing or homogenizing without formation of liposomes or lipospheres.

In certain aspects, an exemplary formulation is as set forth in Table I below, where buprenorphine may be substituted with any active having comparable properties of lipophilicity.

TABLE I

| Component | Formulation | | |
|---|---|---|---|
| | w/w % | w/v % | mg/mL |
| Buprenorphine HCl | 0.611 | 0.58 | 5.8 |
| Capric/caprylic triglycerides | 91.34 | 86.773 | 867.73 |
| Benzyl Alcohol, USP | 1.027 | 0.976 | 9.76 |
| Glycerol tristearate (GTS) | 0.559 | 0.531 | 5.31 |
| Cholesterol, Milled | 6.464 | 6.141 | 61.41 |
| | 100 | 95.00* | 950 |

*Density = 0.95 g/mL

In certain related aspects, an exemplary formulation is as set forth in Table II below, where buprenorphine may be substituted with any active having comparable properties of lipophilicity.

TABLE II

| Component | Formulation | | |
|---|---|---|---|
| | w/w % | w/v % | mg/mL |
| Buprenorphine | 0.611 | 0.58 | 5.8 |
| Capric/caprylic triglycerides | 90.312 | 85.797 | 857.97 |
| Benzyl Alcohol | 2.054 | 1.951 | 19.51 |
| Glycerol tristearate | 0.559 | 0.531 | 5.31 |
| Cholesterol, Micronized | 6.464 | 6.141 | 61.41 |
| | 100 | 95.00* | 950 |

*Density = 0.95 g/mL

In certain aspects, the active is present in an amount of about 0.25 to 0.7% w/w. In other aspects, the triglycerides are caprylic/capric triglycerides or caprylic triglycerides. In other embodiments, the triglyceride is present in an amount of about 85.0% w/w±10.0% w/w. In some preferred aspects, the composition further comprises benzyl alcohol and milled cholesterol, with the latter being about 5.0 to 7.0% w/w and the former being about 1.0 to 2.0, 3.0, 4.0 or 5.0% w/w of the formulation. In other aspects, the composition is formulated for administration by injection.

Also provided herein is a method of treating pain, which may be in a pet animal such as a cat, dog or horse, but any mammal is envisioned for use of the invention, with a single injection of a composition of the invention, requiring only one dose in a single injection for resolution of the pain over a period of at least about 48, 54, 60, 66, 72 hours or greater. No additional dosing for the pain treated should be required (although, of course, re-dosing is possible if a separate incident of pain occurs).

DETAILED DESCRIPTION OF THE INVENTION

Figure 1:
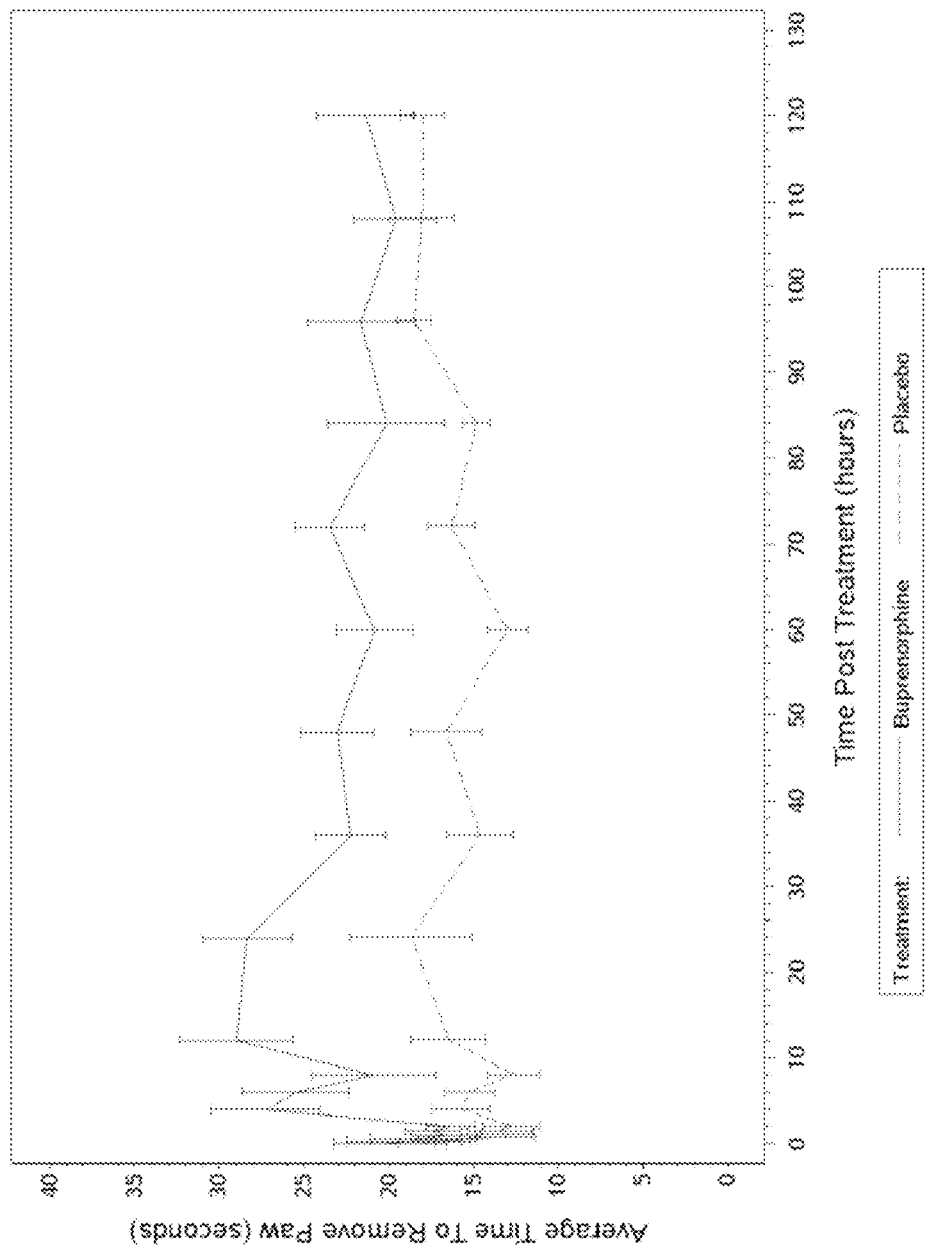
FIG. 1 is a graphical representation depicting data in one embodiment of the invention.

The following terms, definitions and abbreviations apply. Abbreviations used herein have their conventional meaning within the chemical and biological arts.

The term "subject" refers to mammalian organisms to be treated by the methods of the disclosure. Such organisms include, but are not limited to, companion animals such as domestic dogs and cats. In the context of the disclosure, the term "subject" generally refers to an individual who will receive or who has received treatment described below (e.g., administration of the compositions of the disclosure, and optionally one or more additional therapeutic agents).

As used herein, a "patient" or "subject" refers to either a human or non-human mammalian animal. Non-human animals include any non-human mammalian animals. Such non-human animals may include, but are not limited to rodents, non-human primates (e.g., monkey and apes), ungulates, ovines, bovines, ruminants, lagomorphs, porcines, caprines, equines, canines, felines, murines, and the like. In certain embodiments of the invention, the animals are mammals. In some embodiments, the animals include, but are not limited to, companion animals such as domestic dogs and cats. In the context of the disclosure, the term "subject" generally refers to an individual who will receive or who has received treatment described below (e.g., administration of a composition of the disclosure, and optionally one or more additional therapeutic agents).

The term "therapeutically effective amount" means the amount of the compound or pharmaceutical composition that will elicit the biological or medical response of a patient or tissue that is being sought by the researcher, veterinarian, medical doctor or other clinician.

By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the disclosure or pharmaceutical composition to the subject in need of treatment.

The term "about" with respect to a number means that the number includes a range of insignificant variation above and below the number unless otherwise stated; e.g., a value of 1 will be understood to include up to 0.5 to 1.5 and all numbers thereinbetween.

The pharmaceutical compositions of the invention are preferably in the form of a sterile injectable suspension of an active such as buprenorphine or one of comparable lipophilicity, such as those set forth below, in a (i) medium chain triglyceride carrier, preferably a caprylic/capric triglyceride with a (ii) triglyceride miscible solvent and (iii) cholesterol, preferably in micronized and/or milled form.

The triglyceride is present in an amount of about 80.0 to 98.0% w/w, or 85.0 to 95.0% w/w or 90.0 to 95.0% w/w. In some embodiments, the triglyceride is caproic acid, caprylic acid, capric acid, lauric acid, myristic acid or any combination thereof. For example, the triglyceride may be caprylic/capric (C10 and/or C8) triglycerides or caprylic (C8) triglycerides. In embodiments, the triglyceride is a mixture of caprylic acid and capric acid
wherein the mixture comprises about 40.0 to 85.0% caprylic acid and about 15.0 to 60.0% capric acid, or wherein the mixture comprises about 50.0 to 80.0% caprylic acid and about 20.0 to 50.0% capric acid, or wherein the mixture comprises about 65.0 to 80.0% caprylic acid and about 20.0 to 35.0% capric acid, or wherein the mixture comprises about 50.0 to 65.0% caprylic acid and about 30.0 to 45.0% capric acid. In one embodiment, the triglyceride may be a fatty acid ester emollient, such as a saturated coconut and palm kernel oil-derived caprylic/capric fatty acid mixture with glycerin in a solid form sold under the trademark Miglyol™.

The formulation also contains cholesterol particles, preferably in milled form, in an amount of 1.0 to 10.0% w/w of the composition, or 2.0 to 9.0% w/w, or 3.0 to 8.0% w/w or 4.0 to 7.0% w/w or 5.0 to 6.0% w/w, preferably about 6.0% w/w.

Also, while the active molecules may be in their hydrated form, no water is added to the composition during or after mixture. As such, the composition described herein is substantially non-aqueous, for example, the composition has less than about 3.0, 2.5, 2.0, 1.5, 1.0, 0.9, 0.8, 0.7, 0.6, 0.5, 0.4, 0.3, 0.2, 0.1, 0.5 or 0.1% w/w of an aqueous substance, such as water.

An exemplary formulation according to one embodiment of the invention is as follows in Table III, where buprenorphine may be substituted with any active having comparable properties of lipophilicity.

TABLE III

| Formulation | |
|---|---|
| Component | w/w % |
| Buprenorphine HCl | 0.4-1.0 |
| Caprylic/capric triglycerides | 85.0-95.0 |
| Benzyl Alcohol | 0.5-5.0 |
| Glycerol tristearate (GTS) | 0.1-2.5 |
| Cholesterol, Micronized | 1.0-10.0 |
| | 100 |

An exemplary formulation according to one embodiment of the invention is as follows in Table IV, where buprenorphine may be substituted with any active having comparable properties of lipophilicity.

TABLE IV

| Formulation | |
|---|---|
| Component | w/w % |
| Buprenorphine HCl | 0.5-1.0 |
| Caprylic/capric triglycerides | 90.0-92.0 |
| Benzyl Alcohol | 0.5-2.5 |
| Glycerol tristearate (GTS) | 0.1-1.0 |
| Cholesterol, Micronized | 5.0-7.0 |
| | 100 |

An exemplary formulation according to one embodiment of the invention is as follows in Table V, where buprenorphine may be substituted with any active having comparable properties of lipophilicity.

TABLE V

| Formulation | |
|---|---|
| Component | w/w % |
| Buprenorphine HCl | 0.6-0.7 |
| Caprylic/capric triglycerides | 90.0-92.0 |
| Benzyl Alcohol | 2.0 |
| Glycerol tristearate (GTS) | 0.5-0.6 |
| Cholesterol, Micronized | 6.5 |
| | 100 |

An exemplary formulation according to one embodiment of the invention is as follows in Table VI, where buprenorphine may be substituted with any active having comparable properties of lipophilicity.

TABLE VI

| Formulation | | | |
|---|---|---|---|
| Component | w/w % | w/v % | mg/mL |
| Buprenorphine HCl | 0.611 | 0.58 | 5.8 |
| Caprylic/capric triglycerides | 91.34 | 86.773 | 867.73 |
| Benzyl Alcohol | 1.027 | 0.976 | 9.76 |
| Glycerol tristearate (GTS) | 0.559 | 0.531 | 5.31 |
| Cholesterol, Milled | 6.464 | 6.141 | 61.41 |
| | 100 | 95.00* | 950 |

*Density = 0.95 g/mL

An exemplary formulation according to one embodiment of the invention is as follows in Table VII, where buprenorphine may be substituted with any active having comparable properties of lipophilicity.

TABLE VII

| Formulation | | | |
|---|---|---|---|
| Component | w/w % | w/v % | mg/mL |
| Buprenorphine HCl | 0.611 | 0.580 | 5.80 |
| Caprylic/capric triglycerides | 90.312 | 85.797 | 857.97 |
| Benzyl Alcohol | 2.054 | 1.951 | 19.51 |
| Glycerol tristearate (GTS) | 0.559 | 0.531 | 5.31 |
| Cholesterol, Milled | 6.464 | 6.141 | 61.41 |
| | 100 | 95.00* | 950 |

*Density = 0.95 g/mL

The formulation can also contain other inert ingredients such as antioxidants or preservatives. Antioxidants such as a propyl gallate, BHA (butylated hydroxy anisole), BHT (butylated hydroxy toluene) monothioglycerol, tri-ethyl citrate, citric acid, TBHQ (tert-butyl hydroquinone) and the like may be added to the present formulation. The antioxidants are generally added to the formulation in amounts of from about 0.01 to about 2.0% (w/v). Preservatives such as the parabens (methylparaben and/or propylparaben) or benzyl alcohol are suitably used in the formulation in amounts ranging from about 0.01 to about 3.0% w/w.

Without meaning to limit the scope of the invention in any way as to mechanism of action of the compositions of the invention, it is believed that the cholesterol and active ingredients associate with one another in a triglyceride suspension. Having the active proximate to the cholesterol allows the molecules to be brought into intimate association to prolong metabolism of the active out of the bloodstream.

The formulation of the present invention may be prepared by the method described in Example I or Example IV below, all without addition of water to the mixture during any step of the process.

The disclosure also provides pharmaceutical compositions comprising at least one (and preferably only one) active compound in an amount effective for treating a disorder, and a pharmaceutically acceptable vehicle or diluent. For appropriate interaction with the cholesterol components of the invention, the active ingredient should be lipophilic to a degree comparable to buprenorphine. To that end, the buprenorphine noted in any of the formulations herein may be substituted or augmented with any active having similar properties of lipophilicity including, without limitation, anti-inflammatories, analgesics and antibiotics such as marbofloxacin, meloxicam, deracoxib, carprofen, enrofloxacin, cortisone and methyl prednisone.

The active compounds of the disclosure may also be formulated into therapeutic compositions as natural or salt forms. Pharmaceutically acceptable non-toxic salts include the base addition salts (formed with free carboxyl or other anionic groups), which may be derived from inorganic bases such as, for example, sodium, potassium, ammonium, calcium, or ferric hydroxides, and such organic bases as isopropylamine, trimethylamine, 2-ethylamino-ethanol, histidine, procaine, and the like. Such salts may also be formed as acid addition salts with any free cationic groups and will generally be formed with inorganic acids such as, for example, hydrochloric, sulfuric, or phosphoric acids, or organic acids such as acetic, citric, p-toluenesulfonic, methanesulfonic acid, oxalic, tartaric, mandelic, and the like. Salts of the disclosure include amine salts formed by the protonation of an amino group with inorganic acids such as hydrochloric acid, hydrobromic acid, hydroiodic acid, sulfuric acid, phosphoric acid, and the like. Salts of the disclosure may also include amine salts formed by the protonation of an amino group with suitable organic acids, such as p-toluenesulfonic acid, acetic acid, and the like.

Additional excipients which are contemplated for use in the practice of the disclosure are those available to those of ordinary skill in the art, for example, those found in the United States Pharmacopeia Vol. XXII and National Formulary Vol. XVII, U.S. Pharmacopeia Convention, Inc., Rockville, Md. (1989), the relevant contents of which is incorporated herein by reference. In addition, polymorphs, hydrates, and solvates of the compounds are included in the disclosure, with hydrates being particularly preferred. It should be noted that while the hydrate molecules will contribute water to the pharmaceutical composition, it is most preferred that no other water source be included.

In the methods described herein, an appropriate active concentration level will generally be about 1.0 to about 10.0 mg/ml, such as, for example, 0.25 to about 10.0 mg/ml per day, such as 2.5 to about 7.0 mg/ml per day, and also such as 5.0 to 7.0 mg/ml per day (including all intermediate dosages, such as 5.1, 5.2, 5.3, etc. mg/ml preferably about 5.5 to 6.5 mg/ml, all in a single injection form.

Dosing will vary by active drug, species and condition. For example, a suitable dosage level for buprenorphine in dogs is believed to be about 0.1 to 5.0 mg/kg, 0.2 to 4.5 mg/kg, 0.3 to 4.4 mg/kg, 0.4 to 4.3 mg/kg, 0.5 to 4.2 mg/kg and all increments thereinbetween, preferably at least 0.2 mg/kg or higher, such as 0.3 mg/kg.

For the buprenorphine composition in particular, the compounds need only be administered by single subcutaneous injection (preferred for use of higher doses), one time for an entire course of treatment to clinically resolve pain for a duration of at least about 48, 54, 60, 66, 72 or 78 hours. In this respect, "clinically resolve pain" is measured by reference to the clinically significant and measurable presence of the active in the animal's bloodstream (at least about 1.0 ng/ml) for the requisite period of time; e.g., at least about 48, 54, 60, 66, 72 or 78 hours. It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition.

The following examples are provided to further illustrate the embodiments of the present invention, but are not intended to limit the scope of the invention. While they are typical of those that might be used, other procedures, methodologies, or techniques known to those skilled in the art may alternatively be used.

Example I

Formulations

This Example sets forth exemplary formulations of the invention and methods for their preparation.

TABLE VIII

| Formulation | | | |
| --- | --- | --- | --- |
| Master Formula | w/w % | w/v % | mg/mL |
| Buprenorphine HCl, USP | 0.611 | 0.580 | 5.80 |
| Caprylic/Capric Triglycerides, USP (Miglyol ™ 812) | 91.340 | 86.773 | 867.73 |
| Benzyl Alcohol, USP | 1.027 | 0.976 | 9.76 |
| Glyceryl Tristearate (GTS) | 0.559 | 0.531 | 5.31 |
| Cholesterol, Milled | 6.464 | 6.141 | 61.41 |
| Total | 100.0 | 95.00* | 950.0 |

*Density = 0.95 g/mL

Formulation Procedure
1. Charge Miglyol ™ 812 into 2 L flask with screw cap, or suitable formulation vessel, and initiate stirring at 190 rpm.
2. While continuing to stir, add Benzyl Alcohol (from a freshly opened container) to the formulation vessel.
3. Seal flask, stir for 5 minutes.
4. Increase the stirring speed and gradually add Cholesterol (approximately 22 min. duration for addition) to the mixture.
5. Stir mixture for 15 minutes.
6. While continuing to stir, add GTS to mixture.
7. Stir for 5 minutes.
8. While continuing to stir, add Buprenorphine HCl to mixture.
9. Stir for 15 minutes.
10. Pour mixture through a 250 μm screen. Assess screened material as needed.
11. Transfer mixture to a bottle with a screw-cap neck finish, or suitable vessel.
12. Initiate stirring using a magnetic stirrer.
13. Onto the bottle, screw a dispensing pipette that is calibrated to deliver the fill volume (in mL) per stroke.
14. Fill the suspension into glass vials, overlay with nitrogen, then stopper and seal.
15. Terminally sterilize product using e-beam sterilization.

Example II

Pharmacokinetics of a Formulation of the Invention 8 dogs were dosed by subcutaneous injection with the formulation of Example I at a dosing concentration of about 0.2 mg/kg to 1.5 mg/kg. Blood concentrations of buprenorphine were present at clinically significant levels (above about 1 ng/ml) for more than 70 hours following administration of the composition, as shown in FIG. 1.

Example III

Thermal Threshold Testing and Latency

The resistance to pain as a result of the analgesic effect of the inventive compositions is surprisingly prolonged, even when the composition is administered prior to the onset of a pain stimulus. This was demonstrated through a study of 8 dogs dosed as described in Example II followed by, after a 7 day washout period, dosing with a placebo.

The thermal threshold testing and latency (TTL) as a model of pain was measured using a canine thermal escape system, essentially a hot pad onto which the animal's paw is placed. TTL values were measured at 0, 20, 40, 60 and 90 minutes post-treatment, as well as 2, 4, 6, 8, 12, 14, 24, 36, 48, 60, 72, 84, 96, 108 and 120 hours post treatment for all dogs. The time in seconds it took for each dog to remove its paw from the thermal stimulus was recorded three times for each dog at each time point.

The overall treatment effect was statistically significant in the buprenorphine group, in which animals took as much as about 12 minutes longer to withdraw their paw from the thermal stimulus as placebo groups at the same time post-treatment time points, as shown in FIG. 1. Thus animals who received the inventive composition as a single subcutaneous dose were slow to feel and react to the thermal stimulus as dogs in the placebo group. The pain relieving effect was observed over an extended period of time in excess of 72 hours (FIG. 1).

Example IV

Formulations

This Example sets forth exemplary formulations of the invention and methods for their preparation.

TABLE IX

| Formulation | | | |
| --- | --- | --- | --- |
| Master Formula | w/w % | w/v % | mg/mL |
| Buprenorphine HCl, USP* | 0.611 | 0.580 | 5.80 |
| Caprylic/Capric Triglycerides, USP (Miglyol ™ 812)** | 90.312 | 85.797 | 857.97 |
| Benzyl Alcohol, USP, low peroxide, injectable grade | 2.054 | 1.951 | 19.51 |
| Glyceryl Tristearate (GTS), NF (Dynasan ™ 118) | 0.559 | 0.531 | 5.31 |
| Cholesterol, NF, Micronized | 6.464 | 6.141 | 61.41 |
| Total | 100.0 | 95.00*** | 950.0 |

*Added as Buprenorphine HCl, USP; 0.658 w/w %, 0.625 w/v %, 6.25 mg/mL
**Ingredient adjusted to account for API assay
***Density = 0.95 g/mL Formulation Procedure
1. Charge-95% Miglyol ™ 812 into a suitable formulation vessel, and initiate mixing so as to minimize cavitation (approximately 250 rpm).
Note:
Mixing times and speeds are based on a 500 mL batch size, with an A310 impeller.
Mixing times and speeds may be adjusted if a High Shear Mixer is utilized for material incorporation.
2. While continuing to mix, add Benzyl Alcohol (from an unopened or septum-sealed container) to the formulation vessel.
3. Mix until a clear, homogeneous solution results (approximately 20 minutes).
4. Gradually add Cholesterol (approximately 20 minute duration for addition) to the formulation vessel. Decrease the mixing speed to minimize powder kick-off if necessary.
5. Mix until the Cholesterol is fully wetted and evenly dispersed (approximately 45 minutes, 285 rpm).
6. While continuing to mix, add GTS to the formulation vessel. Decrease the mixing speed to minimize powder kick-off if necessary.
7. Mix until the GTS is fully wetted and evenly dispersed (approximately 40 minutes, 285 rpm).
8. While continuing to mix, add Buprenorphine HCl to formulation vessel. Decrease the mixing speed to minimize powder kick-off if necessary.
9. Mix until the Buprenorphine HCl is fully wetted and evenly dispersed (approximately 40 minutes, 285 rpm).
10. Q.S. suspension to final batch weight with Miglyol ™ 812.
11. Pour mixture through a 250 pm screen. Assess screened material as needed.
12. Transfer mixture to a clean, suitable vessel.
13. Initiate mixing so as to maintain an evenly dispersed suspension.
14. With an appropriate device (e.g., pump system), dispense product into suitable containers (e.g., glass vials), ensuring the product remains an evenly dispersed suspension during filling.
15. Overlay with nitrogen, then stopper and seal.
16. Terminally sterilize product using e-beam sterilization.

Example V

Figure 2:
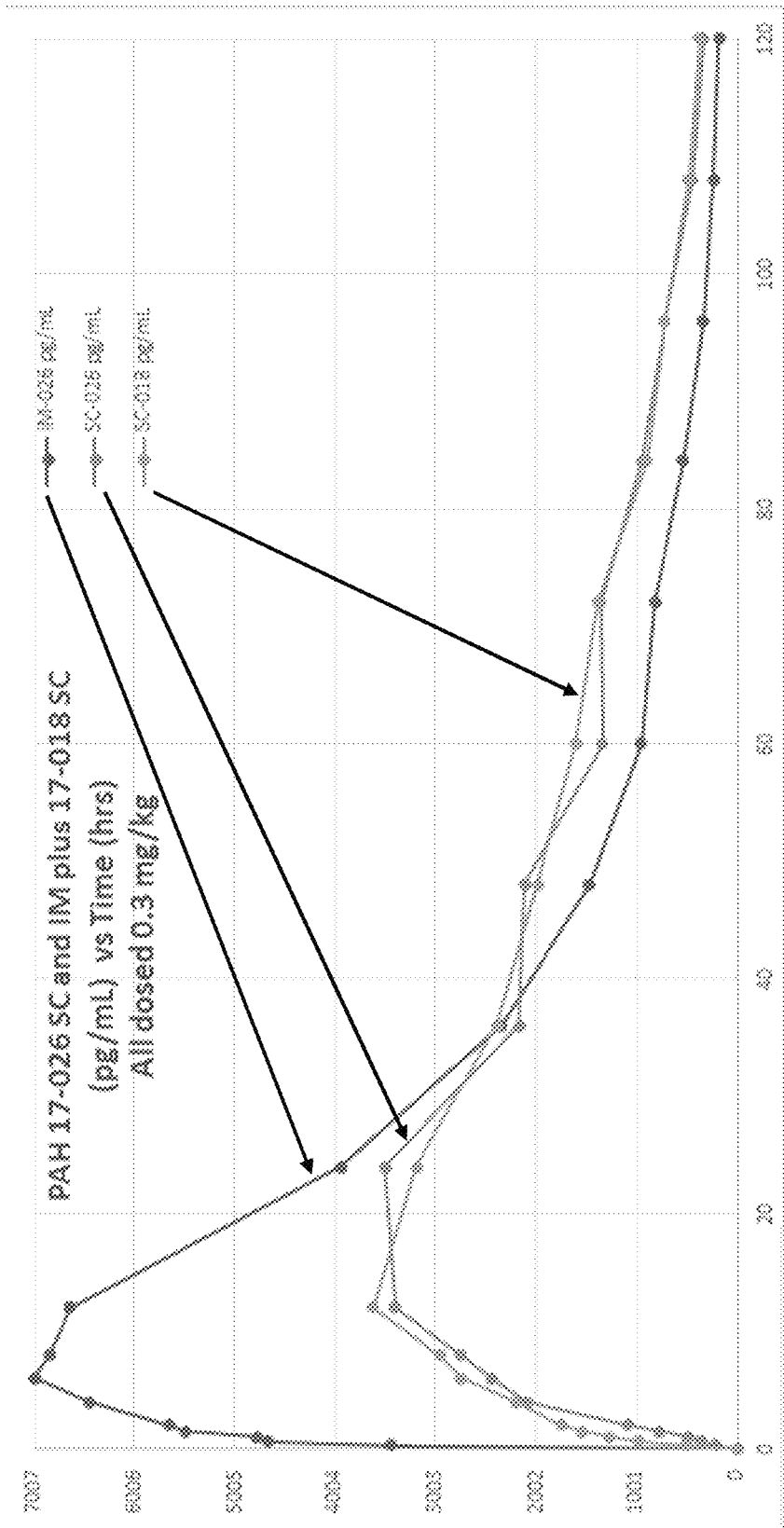
FIG. 2 is a graphical representation depicting data in one embodiment of the invention.

Pharmacokinetics of a Composition of the Invention 20 dogs were dosed by intramuscular injection with the formulation of Example IV (Table IX) at a dosing concentration of 0.3 mg/kg. Blood concentrations of buprenorphine were present at clinically significant levels (above about 1.0 ng/ml) for more than 60 hours following administration of the formulation, as shown in FIG. 2 (IM-026 pg/ml). Also shown in the graph of FIG. 2, are the blood concentrations of buprenorphine upon subcutaneous administration of the formulations of Example IV (Table IX; SC-026 pg/ml) and Example I (Table VIII; SC-018 pg/ml) dosed at 0.3 mg/kg.

Although the objects of the disclosure have been described with reference to the above example, it will be understood that modifications and variations are encompassed within the spirit and scope of the disclosure. Accordingly, the disclosure is limited only by the following claims.

What is claimed is:

1. A long-acting, non-aqueous injectable pharmaceutically acceptable composition, comprising:
   a) a lipophilic active substance, wherein the lipophilic active substance is buprenorphine;
   b) caprylic/capric triglyceride carrier at about 85.0 to 98.0% w/w of the composition;
   c) cholesterol at about 1.0 to 10.0% w/w of the composition;
   d) benzyl alcohol at a concentration of about 0.5 to 5.0% w/w; and
   e) glycerol mono-, di- or tristearate at a concentration of about 0.1 to 2.5% w/w.

2. The composition of claim 1, wherein the composition comprises:
   i) buprenorphine at a concentration of about 0.5 to 1.0% w/w;
   ii) caprylic/capric triglyceride at a concentration of about 90.0 to 92.0% w/w;
   iii) benzyl alcohol at a concentration of about 0.5 to 2.5% w/w;
   iv) cholesterol at a concentration of about 5.0 to 7.0% w/w; and
   v) glycerol tristearate at a concentration of about 0.1 to 1.0% w/w.

3. The composition of claim 1, wherein the composition comprises:
   i) buprenorphine at a concentration of about 0.6-0.7% w/w;
   ii) caprylic/capric triglyceride at a concentration of about 90.0-92.0% w/w;
   iii) benzyl alcohol at a concentration of about 2.0% w/w;
   iv) cholesterol at a concentration of about 6.5% w/w; and
   v) glycerol tristearate at a concentration of about 0.5-0.6% w/w.

4. The composition of claim 1, wherein at least 1.0 ng/ml of active is present in the blood stream of the subject for at least about 48, 54, 60, 66, 72 hours or greater upon administration to a mammal.

5. The composition of claim 1, wherein buprenorphine is present in a dose of about 0.1, 0.2, 0.3, 0.4, 0.5, 1.0, 1.5, 2.0, 2.5, 3.0, 3.5, 4.0, 4.5, 5.0, 5.5, 6.0, 6.5 or 7.0 mg/kg.

6. The composition of claim 1, wherein the buprenorphine is present as the free base (unprotonated) form.

7. The composition of claim 1, wherein the buprenorphine is present as a pharmaceutically acceptable salt.

8. The composition of claim 1, wherein the composition is stable at room temperature for at least 6 months.

9. The composition of claim 8, wherein the composition is stable at room temperature for at least 12 months.

10. A method of treating pain in a subject, comprising administering an effective amount of the composition of claim 1 to the subject to clinically resolve the pain.

11. The method of claim 10, wherein the subject is a mammal.

12. The method of claim 11, wherein the subject is a canine.

13. The method of claim 11, wherein the subject is a feline.

14. The method of claim 10, wherein the composition is administered by subcutaneous injection.

15. The method of claim 10, wherein the composition is administered by intramuscular injection.

16. The method of claim 10, wherein the blood concentration of the lipophilic active substance is greater than about 1 ng/ml for more than about 40, 50, 60, 70 or 80 hours following administration of the composition.

17. The method of claim 16, wherein the lipophilic active substance is buprenorphine.

* * * * *

UNITED STATES PATENT AND TRADEMARK OFFICE
CERTIFICATE OF CORRECTION

PATENT NO. : 10,555,899 B2
APPLICATION NO. : 16/000670
DATED : February 11, 2020
INVENTOR(S) : Douglas I. Hepler, Gail L. Dempsey and Dorothea Erxleben Page 1 of 1

It is certified that error appears in the above-identified patent and that said Letters Patent is hereby corrected as shown below:

On the Title Page

Please correct the listing at (72) Inventors as follows:
Douglas I. Hepler, Greensboro, NC (US)
Gail L. Dempsey, Greensboro, NC (US)
Dorothea Erxleben, Greensboro, NC (US)
Michael Guarnieri Ph.D., Baltimore, MD (US)

Signed and Sealed this
Twenty-first Day of December, 2021

Drew Hirshfeld
*Performing the Functions and Duties of the*
*Under Secretary of Commerce for Intellectual Property and*
*Director of the United States Patent and Trademark Office*